United States Patent [19]
Prevots et al.

[11] Patent Number: 5,712,150
[45] Date of Patent: Jan. 27, 1998

[54] NUCLEIC ACID SEQUENCE AND PLASMIDS COMPRISING AT LEAST ONE PHAGE RESISTENCE MECHANISM, BACTERIA CONTAINING THEM AND THEIR USE

[75] Inventors: Fabien Prevots, Toulouse; Sandrine Tolou; Marléne Daloyau, both of Castanet, all of France

[73] Assignee: Systems Bio-Industries, Boulogne, France

[21] Appl. No.: 689,916

[22] Filed: Aug. 16, 1996

[30] Foreign Application Priority Data

Aug. 18, 1995 [FR] France ............................ 95 09913

[51] Int. Cl.⁶ ............................ C12N 1/21; C12N 15/31
[52] U.S. Cl. ............................ 435/252.3; 536/23.7
[58] Field of Search ............................ 435/252.3; 436/23.7

[56] References Cited

U.S. PATENT DOCUMENTS 4,883,756  11/1989  Klaenhammer et al. ............ 435/252.3

FOREIGN PATENT DOCUMENTS

| 0208468A3 | 1/1987 | European Pat. Off. . |
| 0246909A2 | 11/1987 | European Pat. Off. . |
| 0355036A1 | 2/1990 | European Pat. Off. . |
| 0452224A1 | 10/1991 | European Pat. Off. . |

OTHER PUBLICATIONS

Sanders Phage resistance in lactic acid bacteria. Biochimie vol. 70 pp. 411–421, 1988.
Jarvis et al. Applied and Enviromental Microbiology 55(6): 1537–1543 (1989).
Hill et al. Applied and Enviromental Microbiology 55(7): 1684–1689 (1989).
Steenson et al. Applied and Enviromental Microbiology 50(4): 851–858 (1985).
Steele et al. Plasmid 22:32–43 (1989).
Laible et al. J. Dairy Science 70: 2211–2219 (1987).
Froseth et al. J. Diary Science 71: 275–284 (1986).
Sanders et al. Applied and Enviromental Microbiology 47(5): 979–985 (1984).
Sanders Biochimie 70: 411–421 (1988).
Gautier et al. Applied and Enviromental Microbiology 53(5): 923–927 (1987).
Josephsen et al. Plasmid 23: 71–75 (1990).
Klaenhammer et al. Journal of General Microbiology 131: 1531–1541 (1985).
Coffey et al. Neth. Milk Dairy J 43: 229–244 (1989).
Vlegels et al. Neth. Milk Dairy J. 43: 245–259 (1989).
Sanders et al. Applied and Enviromental Microbiology 46(5): 1125–1133 (1983).
Jarvis et al. Applied and Enviromental Microbiology 54: 777–783 (1988).
Hill et al. Applied adn Enviromental Microbiology 56(7): 2255–2258 (1990).
Prevots et al. Applied and Enviromental Microbiology 56(7): 2180–2185 (1990).
Lerayer Revistra de Microbiologia 20(2): 197–209 (1989).
Klaenhammer J. Dairy Science 72:3426–3443.

*Primary Examiner*—James Ketter
*Assistant Examiner*—John S. Brusca
*Attorney, Agent, or Firm*—Foley & Lardner

[57] ABSTRACT

The invention relates to a polynucleotide of 817 bp comprising at least one phage resistance mechanism and obtainable from the total DNA contained in the *Lactococcus lactis* ssp cremoris strain deposited in the CNCM under No. I-943.

10 Claims, No Drawings

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 817 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Lactococcus lactis ( i x ) FEATURE:
        ( A ) NAME/KEY: CDS
        ( B ) LOCATION:157..690

(xi) SEQUENCE DESCRIPTION: SEQ ID NO: 1:

```
GTAAAAAGTA AAAACGTTAG AAATGGTGAT TTATTTTTCT TTTAATTAAT GATATTATTA        60

GTTAATAAAA TTAATTAGGA GATTTAAGTT GTGAAGGATG TTTTGGATTA TATTATTTCT       120

GGTATAAGTA TATGTATATT TATTTTGGCA GTTAT ATG ATA AAG AAA ATT CCA          174
                                       Met Ile Lys Lys Ile Pro
                                        1               5

GAA ATG GTG AGT GAT AAA TTA AAA AGT GAC AGA GAA TTT GAA TTT AAT         222
Glu Met Val Ser Asp Lys Leu Lys Ser Asp Arg Glu Phe Glu Phe Asn
             10              15                  20

AAG GAG TTA CAG ATT GAT GAA TTT TAT CGA AAA GAT GGG AAT CTG CAA         270
Lys Glu Leu Gln Ile Asp Glu Phe Tyr Arg Lys Asp Gly Asn Leu Gln
         25              30                  35

CAG ATT ATG ATG AAC TGG ACC GAA CTT GCA ATT GAT ACA AAT GCA ATG         318
Gln Ile Met Met Asn Trp Thr Glu Leu Ala Ile Asp Thr Asn Ala Met
     40              45                  50

GAG TCG CTT GAT TCT AAG AAC GGA CAG AAA AAA TTA CGG AAG CTT GTT         366
Glu Ser Leu Asp Ser Lys Asn Gly Gln Lys Lys Leu Arg Lys Leu Val
 55              60                  65                      70

CAA GAA ACA CTT GGA TAT GGT TCA GGA AGA ACA GTT AAA TTA CTA ACA         414
Gln Glu Thr Leu Gly Tyr Gly Ser Gly Arg Thr Val Lys Leu Leu Thr
                 75                  80                  85

GAA ATG CTT CAA GAA AGT TAT CGA AGT AAT GAT ACT GAA TCA GAA AAT         462
Glu Met Leu Gln Glu Ser Tyr Arg Ser Asn Asp Thr Glu Ser Glu Asn
             90                  95                 100

ACT GAA TCA GGA AAT AAT GAA TCA GAA AAT AAT GAA TCT ATA AAT AGG         510
Thr Glu Ser Gly Asn Asn Glu Ser Glu Asn Asn Glu Ser Ile Asn Arg
            105                 110                 115

TCT TCT GCC ACT ATA ATG TTG CTG TTG GCA ATG GTT GTT TCT TCT CTA         558
Ser Ser Ala Thr Ile Met Leu Leu Leu Ala Met Val Val Ser Ser Leu
120                 125                 130

AAG GAA GAT TTT ACT GGA CAA AAA GTT GAC CCA TTA GAT GTC CTT AAA         606
Lys Glu Asp Phe Thr Gly Gln Lys Val Asp Pro Leu Asp Val Leu Lys
135                 140                 145                 150

ATA AAA CTC ACT GAC TAT TAT AAT CAT GAG GGA TTA TTT AAA GAA CTT         654
Ile Lys Leu Thr Asp Tyr Tyr Asn His Glu Gly Leu Phe Lys Glu Leu
                155                 160                 165

TTT GAA AGT GTA AAT AAC AAA CTA GGA GTT GAA GTT TAA TAATGGAAAT          703
Phe Glu Ser Val Asn Asn Lys Leu Gly Val Glu Val
                170                 175

TAATTTTATA GCTCTGGCCT TTGCATCTGT TATTGTAGGT GGGGTATTCA TTGGAATATT       763

TATTCTGGTT TACAAATGGT TGAAGAAATG ATAAGTATAG CTAGACTATG AAAA            817
```

(2) INFORMATION FOR SEQ ID NO: 2:

(i) SEQUENCE CHARACTERISTICS:
        (A) LENGTH: 178 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ile Lys Lys Ile Pro Glu Met Val Ser Asp Lys Leu Lys Ser Asp
 1               5                  10                  15

Arg Glu Phe Glu Phe Asn Lys Glu Leu Gln Ile Asp Glu Phe Tyr Arg
             20                  25                  30

Lys Asp Gly Asn Leu Gln Gln Ile Met Met Asn Trp Thr Glu Leu Ala
         35                  40                  45
```

| Ile | Asp | Thr | Asn | Ala | Met | Glu | Ser | Leu | Asp | Ser | Lys | Asn | Gly | Gln | Lys |
|---|---|---|---|---|---|---|---|---|---|---|---|---|---|---|---|
| | 50 | | | | 55 | | | | | | 60 | | | | |
| Lys | Leu | Arg | Lys | Leu | Val | Gln | Glu | Thr | Leu | Gly | Tyr | Gly | Ser | Gly | Arg |
| 65 | | | | | 70 | | | | 75 | | | | | | 80 |
| Thr | Val | Lys | Leu | Leu | Thr | Glu | Met | Leu | Gln | Glu | Ser | Tyr | Arg | Ser | Asn |
| | | | | 85 | | | | | 90 | | | | | 95 | |
| Asp | Thr | Glu | Ser | Glu | Asn | Thr | Glu | Ser | Gly | Asn | Asn | Glu | Ser | Glu | Asn |
| | | | 100 | | | | | 105 | | | | | 110 | | |
| Asn | Glu | Ser | Ile | Asn | Arg | Ser | Ser | Ala | Thr | Ile | Met | Leu | Leu | Leu | Ala |
| | | 115 | | | | | 120 | | | | | 125 | | | |
| Met | Val | Val | Ser | Ser | Leu | Lys | Glu | Asp | Phe | Thr | Gly | Gln | Lys | Val | Asp |
| | 130 | | | | | 135 | | | | | 140 | | | | |
| Pro | Leu | Asp | Val | Leu | Lys | Ile | Lys | Leu | Thr | Asp | Tyr | Tyr | Asn | His | Glu |
| 145 | | | | | 150 | | | | | 155 | | | | | 160 |
| Gly | Leu | Phe | Lys | Glu | Leu | Phe | Glu | Ser | Val | Asn | Asn | Lys | Leu | Gly | Val |
| | | | | 165 | | | | | 170 | | | | | 175 | |
| Glu | Val | | | | | | | | | | | | | | |

( 2 ) INFORMATION FOR SEQ ID NO: 3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: misc_signal
        ( B ) LOCATION:6..11
        ( D ) OTHER INFORMATION:/function="EcoRI restriction
            site"

( i x ) FEATURE:
        ( A ) NAME/KEY: misc_structure
        ( B ) LOCATION:12..31
        ( D ) OTHER INFORMATION:/function="sequence homologous to
            nucleotides 1-20 of SEQ ID NO:1"

( x i ) SEQUENCE DESCRIPTION: SEQ ID NO: 3:

TACGTGAATT CGTAAAAAGT AAAAACGTTA G        31

( 2 ) INFORMATION FOR SEQ ID NO: 4:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: misc_signal
        ( B ) LOCATION:6..11
        ( D ) OTHER INFORMATION:/function="EcoRI restriction
            site"

( i x ) FEATURE:
        ( A ) NAME/KEY: misc_structure
        ( B ) LOCATION:12..31
        ( D ) OTHER INFORMATION:/function="sequence homologous to
            the cDNA corresponding to nucleotides 789-817
            of SEQ ID NO:1"

( x i ) SEQUENCE DESCRIPTION: SEQ ID NO: 4:

```
TACGTGAATT CTTTTCATAG TCTAGCTATA C                                31
```

NUCLEIC ACID SEQUENCE AND PLASMIDS COMPRISING AT LEAST ONE PHAGE RESISTENCE MECHANISM, BACTERIA CONTAINING THEM AND THEIR USE

The present invention relates to a novel nucleic acid sequence and plasmids capable of hybridizing therewith and carrying at least one phage resistance mechanism, to the lactic acid bacteria containing this sequence or these plasmids, in particular the lactococci belonging to the species *Lactococcus lactis*, to the use of certain strains of these lactococci for transferring a phage resistance mechanism, especially by conjugation, to strains of industrial interest, particularly in the dairy industry, and to the use of certain strains of *Lactococcus lactis* for obtaining these plasmids.

Lactic acid bacteria are involved in the production and preservation of a large number of foodstuffs such as cheeses, butter, yogurts, sausage or sauerkraut. Among these, dairy products occupy a particularly important position. The industrial conversion of milk is carried out in ever larger fermentation vats, in which the appearance of phages of lactic acid bacteria can have serious or even catastrophic consequences, namely a variation in the characteristics, especially organoleptic characteristics, of the final product, a loss of product present in the vat, and the need to decontaminate the latter as well as the surrounding installations. The dairy industry is therefore in urgent need of novel means and novel methods of rendering lactic acid bacteria more resistant to phages.

The phages of lactic acid bacteria belong to three major homology groups (I), (II) and (III) defined by DNA/DNA hybridization studies according to RELANO P. et al., (1987), J. Gen. Microbiol. 133, 3053–3063. Groups (I) and (III) comprise only virulent phages. Group (II) comprises virulent phages and temperate phages. The homologics are strong within one and the same group and very weak between groups. The phages of group (I) have an oblong nucleocapsid while the phages of groups (II) and (III) have an isometric nucleocapsid.

Several natural phage resistance mechanisms are known to exist, the three main ones being:

inhibition of phage adsorption; in this mechanism, the adsorption of the phage by the bacterium is inhibited or delayed.

the restriction/modification system; this system involves a restriction enzyme, which degrades the DNA of the phage as soon as it enters the bacterium.

abortive infection; according to this third mechanism, phage adsorption is normal but phage multiplication does not take place.

These mechanisms are described in detail by SANDERS M. in Biochimie 70, (1988), 411–421.

The development of phage resistant lactic acid bacteria has already been the subject of numerous studies.

In this connection, reference may be made to the following articles in particular:

VLEGELS et al.; Neth. Milk and Dairy J. 43, (1989), 245–259;

SANDERS and KLAENHAMMER; Applied and Environ. Microbiol. (1983), vol. 46, 1125–1133;

these articles relate to plasmids which inhibit phage adsorption;

Audrey W. JARVIS; Applied and Environ. Microbiol.; March 1988, p. 777–783;

EP-A3-0 208 468;

COFFEY et al.; Neth. Milk and Dairy J. 43, (1989), 229–244;

KLAENHAMMER and SANOZKY; Journal of General Microbiol. (1985), 131, 1531–1541;

DURMAZ et al.; J. Bact. (1992), 7463–7469;

McLANDSBOROUGH et al.; Applied and Environ. Microbiol. (1995), 2023–2026;

these articles describe plasmids which confer phage resistance by the abortive infection mechanism;

JOSEPHSEN and KLAENHAMMER, Plasmid 23, 71–75, (1990);

MOINEAU et al.; Applied and Environ. Microbiol. (1995), 2193–2202;

U.S. Pat. No. 4,883,756;

GAUTIER and CHOPIN; Applied and Environ. Microbiol. (1987), 53, p. 923–927;

these last articles describe especially plasmids which confer phage resistance by the restriction/modification mechanism.

Patent application EP-A1-452 224 also describes a DNA sequence comprising at least one phage resistance mechanism; this DNA sequence contains a functional portion of the HindIII-HindIII fragment of about 3.3 kb of plasmid pPF144-1 present in the *Escherichia coli* strain deposited on 9th Apr. 1991 in the CNCM (Collection Nationale de Cultures de Microorganismes, Institut Pasteur, Paris, France) under no. I-1070.

This HindIII-HindIII fragment of about 3.3 kb was isolated from plasmid pPF144 contained in the *Lactococcus lactis* ssp lactis strain deposited in the CNCM on 12th Apr. 1990 under no. I-945, which is a transconjugant resulting from the crossing of the donor strain *Lactococcus lactis* ssp lactis S91, deposited in the CNCM on 12th Apr. 1990 under no. I-940, and the recipient strain *Lactococcus lactis* ssp lactis S45, derived from the strain *Lactococcus lactis* ssp lactis C2-LL described by McKay et al., 1977, in J. Bacteriol. 257–265. This fragment carries one or more phage resistance mechanisms.

Following this work, a DNA sequence of 1.9 kb which by itself confers phage resistance was isolated from this HindIII-HindIII DNA sequence of 3.3 kb. This novel DNA sequence of about 1.9 kb was described in EP-A1-643 134.

The Applicant has now isolated a DNA fragment of 7.276 kb from the genome of the phage resistant strain *Lactococcus lactis* ssp cremoris S114, deposited in the CNCM on 12th Apr. 1990 under no. I-943, by partial digestion with the restriction enzyme Sau3A. This DNA fragment by itself confers phage resistance and carries one or more phage resistance mechanisms. It has been entirely sequenced. From this sequence of 7.276 kb, the Applicant subsequently isolated a DNA sequence of 817 bp which by itself confers phage resistance.

The present invention therefore relates to a novel nucleic acid sequence comprising at least one phage resistance mechanism, said sequence containing 817 bp and consisting of:

a) the DNA sequence having the nucleic acid series of [SEQ ID No. 1];

b) the DNA sequences hybridizing with the above sequence or a fragment thereof; and c) the corresponding mRNA and cDNA sequences.

The sequence [SEQ ID No. 2] is the amino acid sequence deduced from the sequence [SEQ ID No. 1].

The DNA sequence [SEQ ID No 1] can be obtained by the PCR method using the following two oligonucleotides:

5'TACGTGAATTCGTAAAAAGTAAAAACGTTAG3'
       <u>EcoRI</u>

-continued oligonucleotide D [SEQ ID No.4]:

5'TACGTGAATTCTTTTCATAGTCTAGCTATAC3'
    EcoRI

The invention particularly relates to the DNA sequence comprising at least one phage resistance mechanism having the sequence [SEQ ID No 1].

The invention further relates to the DNA sequences which have a high degree of homology with the DNA sequence [SEQ ID No. 1] above. Here a high degree of homology means a homology (ratio of the identical nucleotides to the total number of nucleotides) of at least 70%, preferably at least 80%, of the nucleotide sequences when they are aligned according to the maximum homology by the optimal sequence alignment method of Needleman and Wunsch, 1970, J. Mol. Biol. 48, 443–453. This method is used especially in the UWGCG software of the University of Wisconsin: Devereux et al., 1984, Nucl. Ac. Res. 12, 8711–8721—option GAP.

The present invention particularly relates to the DNA sequences which hybridize with the DNA sequence [SEQ ID No1] or a fragment thereof. In the present specification the term "hybridization" designated the conventional hybridization conditions and more particularly the stringent hybridization conditions.

The invention further relates to the plasmids transformed with one of the nucleic acid sequences according to the invention. A possible example of these plasmids is plasmid pLAB205 into which the DNA sequence according to the invention has been cloned by the customary techniques known to those skilled in the art.

The invention further relates to the phage resistant lactic acid bacteria, preferably belonging to the species *Lactococcus lactis*, which contain at least one DNA sequence or one plasmid as defined above.

This nucleic acid sequence or this plasmid may have been introduced into the lactic acid bacteria by conjugation, transformation, protoplast fusion or any other gene transfer method well known to those skilled in the art.

The lactic acid bacteria which can advantageously be transformed with the nucleic acid sequence according to the invention, or a plasmid containing it, are for example the strains of *Lactococcus lactis* ssp cremoris, *Lactococcus lactis* ssp lactis and *Lactococcus lactis* ssp lactis var. diacetylactis.

These strains transformed in this way can be used for transmitting a phage resistance mechanism to a strain of industrial interest by conjugation, transformation, transduction, protoplast fusion or any other gene transfer method well known to those skilled in the art. This mechanism can be carried by a plasmid or by another part of the bacterial genome. If it is carried by a plasmid, it is advantageously transferred by conjugation.

The invention further relates to the phage resistant strains of industrial interest obtained in this way.

The invention will be understood more clearly with the aid of the following Examples, which comprise experimental results and a discussion thereof. Some of these Examples relate to experiments performed for the purpose of carrying out the invention; others relate to embodiments of the invention, which are of course given purely by way of illustration.

The majority of the techniques described in these Examples, which are well known to those skilled in the art, are explained in detail in the work by Sambrook, Fritsch and Maniatis entitled "Molecular cloning; a Laboratory Manual", published in 1989 by Cold Spring Harbor Press, New York (2nd edition).

EXAMPLE 1

Preparation of the fragment of 7.276 kb

The strain *Lactococcus lactis* ssp cremoris S114, deposited in the CNCM under no. I-943 on 12th Apr. 1990, contains one or more phage resistances. In particular, it has transferred plasmid pPF66 by conjugation into the recipient strain *Lactococcus lactis* S45, derived from the strain *Lactococcus lactis* C2-LL described by McKay et al., 1977, J. Bacteriol. 257–265, said plasmid conferring resistance to phages Ø 53 (group I) and Ø 59 (group III). Other phage resistance mechanisms may be present in the strain I-943. It is for this reason that a DNA library was constructed from the genome of the strain I-943.

The DNA of the strain I-943 was extracted and partially digested with the restriction enzyme Sau3A. Plasmid pLDP1 was used. Plasmid pLDP1 is derived from plasmid pVA838 (Macrina F. L. et al., Gene 19, 345–353) by deletion of the 1523 bp fragment between the HindIII site (0) and the EcoRI site (1523) and replacement thereof with 54 base pairs corresponding to the multiple cloning sites of plasmid pUC18 (Yanisch-Perron C. et al.: 1985—Gene 33, 103–119) which are flanked by EcoRI-HindIII. Plasmid pLDP1 is digested at the BamHI site and the sticky ends are dephosphorylated with alkaline phosphatase. The mixture of plasmid and Sau3A fragments is ligated with T4 DNA ligase and is used for transforming the strain *E. coli* TG1 (selection on LB medium+erythromycin 200 µg/ml). 100,000 clones are obtained.

The 100,000 clones were mixed and the total plasmid DNA was extracted and used for transforming the strain *Lactococcus lactis* MG1363, which is disclosed by GASSON M. J. (1983) in J. Bacteriol. 154: 1–9, hereinafter named strain *L. lactis* S56 or S56. The transformants were plated on dishes of M17+erythromycin 5 µg/ml+glucose 0.5% at a rate of 500 clones per dish and left in the oven at 30° C. for 30 h. M17 medium is described by TERZAGHI et al. (1975) in Appl. Environ. Microbiol. 29, 807–813. These clones were then replicated by the velvet replication technique on dishes of M17+glucose 0.5%, on which $10^8$ phages Ø 59 (group III) were plated per dish. Out of 3600 clones tested by this process, 6 clones resistant to phage Ø 59 were found. One of these clones was tested by phage typing and shows a total resistance to Ø 59 and a partial resistance to Ø 53. Plasmid pLDP1 present in this clone contains a fragment of about 7.5 kb. This new plasmid, comprising pLDP1 and this fragment of about 7.5 kb, was called pLAB201. The nucleic acid sequence of this fragment was determined by the method of Sanger et al. (PNAS - USA, 14, 5463 - 1977); it has a size of 7.276 kb.

Analysis of the sequence showed that this fragment of 7.276 kb possesses 10 open reading frames (ORF) with a size of more than 300 base pairs.

EXAMPLE 2

Treatment with Exonuclease BAL31

A unique SalI digestion site is present in pLDP1, next to ORF1. Plasmid pLAB201 was digested with SalI and treated with exonuclease BAL31. The DNA treated with BAL31 was religated with T4 DNA ligase and retransformed TG1 (selection with erythromycin 200 µg/ml). All the plasmids obtained were extracted and used for transforming S56

(selection with erythromycin 5 μg/ml). Comparisons were made between the size and location of the BAL31 deletion and the loss or maintenance of the resistance phenotype. The phage resistance is found to disappear when the open reading frame called ORF7 is deleted.

EXAMPLE 3

Amplification of an Internal Fragment of the 7.276 kb Fragment by PCR

The PCR (Polymerase Chain Reaction) technique, described for example in the work by Maniatis cited above, makes it possible to amplify a DNA fragment contained between two appropriately chosen oligonucleotides. This amplified DNA can easily be cloned if restriction sites are provided by the oligonucleotides. In fact, the sequences of these oligonucleotides can contain, at their 5' end, a heterologous part of the DNA to be amplified, consisting of 10 to 12 base pairs, for example, 6 of which constitute a restriction site.

The following oligonucleotides were synthesized in this Example:

oligonucleotide D [SEQ No. 4]:

5'TACGTGAATTCTTTTCATAGTCTAGCTATAC3'
    EcoRI oligonucleotide E [SEQ No. 3]:

5'TACGTGAATTCGTAAAAAGTAAAAACGTTAG3'
    EcoRI

The oligonucleotides E and D made it possible to amplify a DNA fragment of 817 bp containing ORF7.

This DNA was amplified in the form of an EcoRI-EcoRI fragment by virtue of the restriction sites provided by the oligonucleotides, enabling cloning into shuttle plasmid pLDP1.

This DNA fragment was amplified by PCR starting from the total DNA of the strain I-943. The PCR products were purified by phenol/chloroform extraction, digested with EcoRI and cloned into vector pLDP1.

Cloning of the fragments into pLDP1 enabled them to be introduced into the strain *L. lactis* S56, after amplification of the recombinant plasmids in the strain *E. coli* TG1, and to determine whether they confer phage resistance.

EXAMPLE 4

Phage Resistance Conferred by the 817 bp Fragment

Plasmids pLAB205 and pLDP1 were introduced into the strain *L. lactis* S56. The phage resistance of the clones obtained was tested by performing a titration (PFU/ml) with phages ∅ 53 and ∅ 59.

The results are given below:

| Strain | Phage ∅ 53 (I) | | Phage ∅ 59 (III) | |
|---|---|---|---|---|
| | Titer | Size of the plaques (mm) | Titer | Size of the plaques (mm) |
| S56 | $4 \times 10^9$ | 3 | $6 \times 10^6$ | 2 |
| S56 (pLDP1) | $4 \times 10^9$ | 3 | $4 \times 10^6$ | 2 |
| S56 (pLAB205) | $2 \times 10^6$ | 0.5 | $6 \times 10^3$ | 0.5 |

PFU/ml = plate forming units per ml

What is claimed is:

1. A polynucleotide comprising at least one phage resistance mechanism, said polynucleotide selected from the group consisting of:
   (a) a DNA having the nucleic acid sequence of SEQ ID NO. 1;
   (b) a DNA having at least 70% homology with (a); and
   (c) the corresponding mRNA and cDNA polynucleotide of (a) or (b).

2. A polynucleotide according to claim 1, wherein the polynucleotide is at least 70% homologous with said sequence of (a).

3. A plasmid comprising at least one phage resistance mechanism and containing a polynucleotide according to claim 1.

4. A plasmid comprising at least one phage resistance mechanism and containing a polynucleotide according to claim 2.

5. A phage resistant lactic acid bacterium which contains at least one plasmid according to claim 3.

6. A phage resistant lactic acid bacterium which contains at least one plasmid according to claim 4.

7. A method of conferring phage resistance to a bacterium, comprising
   introducing a plasmid according to claim 3 into the bacterium.

8. A method of conferring phage resistance to a bacterium, comprising
   introducing a plasmid according to claim 4 into the bacterium.

9. A polynucleotide according to claim 1, wherein the DNA of (b) has at least 80% homology with (a).

10. A polynucleotide according to claim 2, wherein the polynucleotide is at least about 80% homologous with said sequence of (a).

* * * * *